US009449786B2

(12) United States Patent
Tsuchiya et al.

(10) Patent No.: US 9,449,786 B2
(45) Date of Patent: Sep. 20, 2016

(54) CHARGED PARTICLE RADIATION DEVICE AND SPECIMEN PREPARATION METHOD USING SAID DEVICE

(71) Applicant: Hitachi High-Technologies Corporation, Minato-ku, Tokyo (JP)

(72) Inventors: Miki Tsuchiya, Tokyo (JP); Yasuhira Nagakubo, Tokyo (JP); Satoshi Tomimatsu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/786,446

(22) PCT Filed: Apr. 11, 2014

(86) PCT No.: PCT/JP2014/060457
§ 371 (c)(1),
(2) Date: Oct. 22, 2015

(87) PCT Pub. No.: WO2014/175074
PCT Pub. Date: Oct. 30, 2014

(65) Prior Publication Data
US 2016/0071687 A1 Mar. 10, 2016

(30) Foreign Application Priority Data

Apr. 23, 2013 (JP) .................................. 2013-090241

(51) Int. Cl.
*H01J 37/20* (2006.01)
*H01J 37/305* (2006.01)
(Continued)

(52) U.S. Cl.
CPC .................. *H01J 37/20* (2013.01); *B25J 7/00* (2013.01); *G01N 1/42* (2013.01); *H01J 37/28* (2013.01);
(Continued)

(58) Field of Classification Search
USPC .......... 250/306, 307, 309–311, 398, 550.11, 250/442.11, 443.11, 492.1, 492.2, 492.3, 250/526
See application file for complete search history.

(56) References Cited

U.S. PATENT DOCUMENTS 5,270,552 A 12/1993 Ohnishi et al.
6,410,925 B1 6/2002 Armbruster et al.
(Continued)

FOREIGN PATENT DOCUMENTS

JP 5-52721 A 3/1993
JP 2002-144298 A 5/2002
(Continued)

OTHER PUBLICATIONS

International Search Report (PCT/ISA/210) issued in counterpart International Application No. PCT/JP2014/060457 dated Jul. 15, 2014, with English translation (Four (4) pages).
(Continued)

*Primary Examiner* — Bernard Souw
(74) *Attorney, Agent, or Firm* — Crowell & Moring LLP

(57) ABSTRACT

The present invention enables a sample to be observed in a clean state directly after preparation of a final observation surface when preparing a sample for observing a material that is sensitive to heat. The present invention is a method of preparing a sample using a charged particle beam device including a microprobe having a cooling mechanism, a first sample holder having a mechanism for retaining a sample in a cooled state, and a stage into which the microprobe and the first sample holder can be introduced, the method including cutting a bulk-shaped sample piece from the sample on the first sample holder retained in a cooled state; adhering the sample piece to a distal end of the microprobe that is cooled to a fixed temperature and transferring the sample piece to a second sample holder for thin film observation retained in a cooled state, which is different from the first sample holder, within a vacuum chamber of the charged particle beam device; separating the sample piece that has been transferred to the second sample holder from the microprobe and thin film processing the sample piece to a thickness that is less than the thickness during cutting; and observing the sample piece after the thin film processing.

13 Claims, 15 Drawing Sheets

(51) Int. Cl.

| | |
|---|---|
| *G01N 1/42* | (2006.01) |
| *H01J 37/302* | (2006.01) |
| *H01J 37/304* | (2006.01) |
| *B25J 7/00* | (2006.01) |
| *H01J 37/28* | (2006.01) |
| *H01J 37/30* | (2006.01) |
| *G01N 1/28* | (2006.01) |

(52) U.S. Cl.
CPC .............. *H01J 37/30* (2013.01); *H01J 37/302* (2013.01); *H01J 37/304* (2013.01); *H01J 37/3056* (2013.01); *G01N 2001/2873* (2013.01); *H01J 2237/002* (2013.01); *H01J 2237/2001* (2013.01); *H01J 2237/202* (2013.01); *H01J 2237/2007* (2013.01); *H01J 2237/208* (2013.01); *H01J 2237/2801* (2013.01); *H01J 2237/30461* (2013.01); *H01J 2237/31745* (2013.01); *H01J 2237/31749* (2013.01)

(56) References Cited

U.S. PATENT DOCUMENTS

| | | |
|---|---|---|
| 6,916,314 B2 * | 7/2005 | Schneider ........ A61B 17/00234 606/1 |
| 9,142,384 B2 * | 9/2015 | Schampers .............. G01N 1/28 |
| 2004/0262516 A1 | 12/2004 | Motoi et al. |
| 2006/0113488 A1 | 6/2006 | Motoi |
| 2008/0290290 A1 | 11/2008 | Nagakubo et al. |
| 2012/0112064 A1 * | 5/2012 | Nagakubo .............. G01N 1/286 250/307 |

FOREIGN PATENT DOCUMENTS

| | | |
|---|---|---|
| JP | 2004-508661 A | 3/2004 |
| JP | 2004-227842 A | 8/2004 |
| JP | 2005-148003 A | 6/2005 |
| JP | 2006-73270 A | 3/2006 |
| JP | 2006-196310 A | 7/2006 |
| JP | 2008-288161 A | 11/2008 |
| JP | 2010-55988 A | 3/2010 |
| JP | 2010-257617 A | 11/2010 |
| JP | 2011-129441 A | 6/2011 |
| WO | WO 2010/122717 A1 | 10/2010 |
| WO | WO 2012/008089 A1 | 1/2012 |

OTHER PUBLICATIONS

Japanese Society of Electron Microscopy—Kanto Branch: "Electron Microscopy Biological Sample Preparation Method", Maruzen Co., Ltd., 1986, pp. 267-270, with "Concise Explanation" in English (Five (5) pages).

* cited by examiner

CHARGED PARTICLE RADIATION DEVICE AND SPECIMEN PREPARATION METHOD USING SAID DEVICE

TECHNICAL FIELD

The present invention relates to a charged particle beam device having a charged particle source (for example, an ion source or an electron beam source) as well as a sample preparation method using the device.

BACKGROUND ART

Recently, Scanning Electron Microscopy (hereinafter referred to as "SEM"), Transmission Electron Microscopy (hereinafter referred to as "TEM"), or Scanning Transmission Electron Microscopy (hereinafter referred to as "STEM") are often used to analyze a sample having a fine structure. Before introducing a sample into these observation devices, it is necessary to prepare a cross section or thin film of the sample, and thus a Focused Ion Beam (hereinafter referred to as "FIB") device is used. A method for FIB processing an observation portion into a thin film shape is called FIB microsampling, and this is the most suitable sample preparation method when using electron microscopy and the like to analyze the condition/structure on the order of several nm, which is the subject of recent nanotechnology research (PTL 1).

In processing or observation of a sample using a charged particle beam device, the temperature of the sample rises due to the energy of the charged particle beam, and there are cases in which it can be difficult to analyze the original structure of the sample. Thus, a method of processing or observing a sample using a charged particle beam device while cooling the sample has been proposed (PTL 2).

Further, in the procedure for preparing a thin film sample in order to observe the cooled sample with a TEM device or STEM device, a method of using a cooled manipulator to remount a sample with a thin film shape prepared on a base material onto a cooling sample holder has been proposed as disclosed in PTL 4.

In addition, among methods for preparing a cross section of a material that is sensitive to heat such as a liquid sample, a biological sample, or a polymer material without using a FIB device, a method of cutting a frozen sample with a cooled knife such as freeze etching is known (NPL 1).

CITATION LIST

Patent Literature

PTL 1: JP 05-52721 A
PTL 2: JP 2010-257617 A
PTL 3: JP 2004-508661 W
PTL 4: JP 2010-55988 A

Non-Patent Literature

NPL 1: Japanese Society of Electron Microscopy—Kanto Branch: Electron Microscopy Biological Sample Preparation Method (Maruzen Co., Ltd., 1986) P. 267

SUMMARY OF INVENTION

Technical Problem

When processing and observing a liquid sample or biological cell that includes water using a charged particle beam device, the sample is prepared using a pretreatment method such as a quick freezing method. Therein, the sample is mounted on a sample holder than can be maintained in a frozen state and then introduced into the charged particle beam device. Further, when observing such a sample with a charged particle beam device for observation such as a TEM or STEM device, it is necessary to prepare a thin film of the sample. When preparing a thin film of a frozen sample prepared using the above-described quick freezing method or the like, a cryo-microtome method using a cooled knife is employed. However, there has been a problem in that in the cryo-microtome method, the processing position accuracy relative to the desired portion of observation is poor.

In order to improve the processing position accuracy, it has become possible to extract the desired portion of observation to prepare a thin film sample by using a microprobe incorporated in the FIB device as disclosed in PTL 1. However, in this method, the microprobe does not include a cooling mechanism and is at ambient temperature. Thus, when extracting the sample, it is necessary to return the thin film sample prepared in a cooled state using the cryo-microtome method to ambient temperature. Further, after re-cooling the sample that was returned to ambient temperature, the sample is irradiated with a FIB for thin film processing, and then observed with STEM or TEM. Therefore, damage or throughput degradation may occur due to temperature changes of the sample.

If a sample such as a frozen sample is mounted in a cooled state in a processing device or observation device, frost can adhere to the sample surface during processing or observation. In order to prevent the adherence of frost, a sample holder having a frost adherence prevention cover such as the cryoshutter disclosed in PTL 3 has been proposed. However, this frost adherence prevention cover is effective during holder transport outside of a vacuum device. In order to remove frost that has adhered after transport into a vacuum device, it is necessary to raise the sample temperature to about −90° C., which is the sublimation temperature of frost in a vacuum state. However, there has been a problem in that this temperature increase causes also amorphous ice in the frozen sample to sublime simultaneously with the frost, and thus the quality of the sample may degenerate and the sample may deform, and the temperature adjustment may take time.

Thus, a system as disclosed in PTL 4 in which a cooling manipulator is used to extract a thin film sample and mount the extracted thin film sample on a separate stage has been proposed. However, this system is a method for extracting a sample that has been thin film processed on a base material, and thus the uses thereof are limited. Further, when extracting the thin film sample or mounting on a separate sample stage, it is necessary to adhere the cooling manipulator and the thin film sample to each other and adhere the separate sample stage and the thin film sample to each other. However, the final observation surface may be contaminated during movement of the thin film sample. In general, a thin film sample prepared for STEM or TEM observation has a film thickness in the observation direction of several hundred nanometers or less. On the other hand, a sample piece or bulk-shaped sample that is handled in the invention explained in the present specification indicates a sample having a thickness in the observation direction of several micrometers.

In addition, when observing a cross section of a frozen sample as described above, there is a method in which a cross section is prepared using a FIB device and then observed. However, thermal damage caused by ion beam irradiation during cross section preparation may occur on the sample cross section, and it is conceivable that the original structure of the sample may be unable to be confirmed. In a frozen cutting method, a frozen sample is directly cut, and thus it is possible to observe a condition that is close to the original sample structure. There is also a need to make observations by comparing both an ion beam processed cross section and a frozen cut cross section, but at present, the throughput is poor because the FIB processed cross section and the frozen cut cross section must be prepared in different devices.

As discussed above, there are various problems in the conventional devices and methods. However, the present specification provides a sample preparation method and a charged particle beam device in which a sample can be observed in a clean state directly after preparation of the final observation surface when preparing a sample for observing at least a material that is sensitive to heat.

Solution to Problem

In order to solve the above-mentioned problem, the present specification provides multiple means. As one of the means, the present invention provides a method of preparing a sample using a charged particle beam device including a microprobe having a cooling mechanism, a first sample holder having a mechanism for retaining a sample in a cooled state, and a stage into which the microprobe and the first sample holder can be introduced, the method including: cutting a bulk-shaped sample piece from the sample on the first sample holder retained in a cooled state; adhering the sample piece to a distal end of the microprobe that is cooled to a fixed temperature and transferring the sample piece to a second sample holder for thin film observation retained in a cooled state, which is different from the first sample holder, within a vacuum chamber of the charged particle beam device; separating the sample piece that has been transferred to the second sample holder from the microprobe and thin film processing the sample piece to a thickness that is less than the thickness during cutting; and observing the sample piece after the thin film processing.

Advantageous Effects of Invention

According to the present invention, a sample in a frozen state retained on a first sample holder can be suspended as is in a bulk shape and then remounted on a second sample holder for thin film observation that is retained in a cooled state to prepare a thin film. Therefore, a thin film sample in which a desired portion of observation has been processed with high accuracy can be prepared without degrading the quality of the sample or contaminating the sample. Thereby, even a material that is sensitive to heat can be stably processed and observed while being maintained in its original shape. Problems, constitutions, and effects other than those explained above will be clarified by the explanations of the embodiments below.

DESCRIPTION OF EMBODIMENTS

Embodiments are hereinafter described with reference to the drawings.

Embodiment 1

Figure 1:
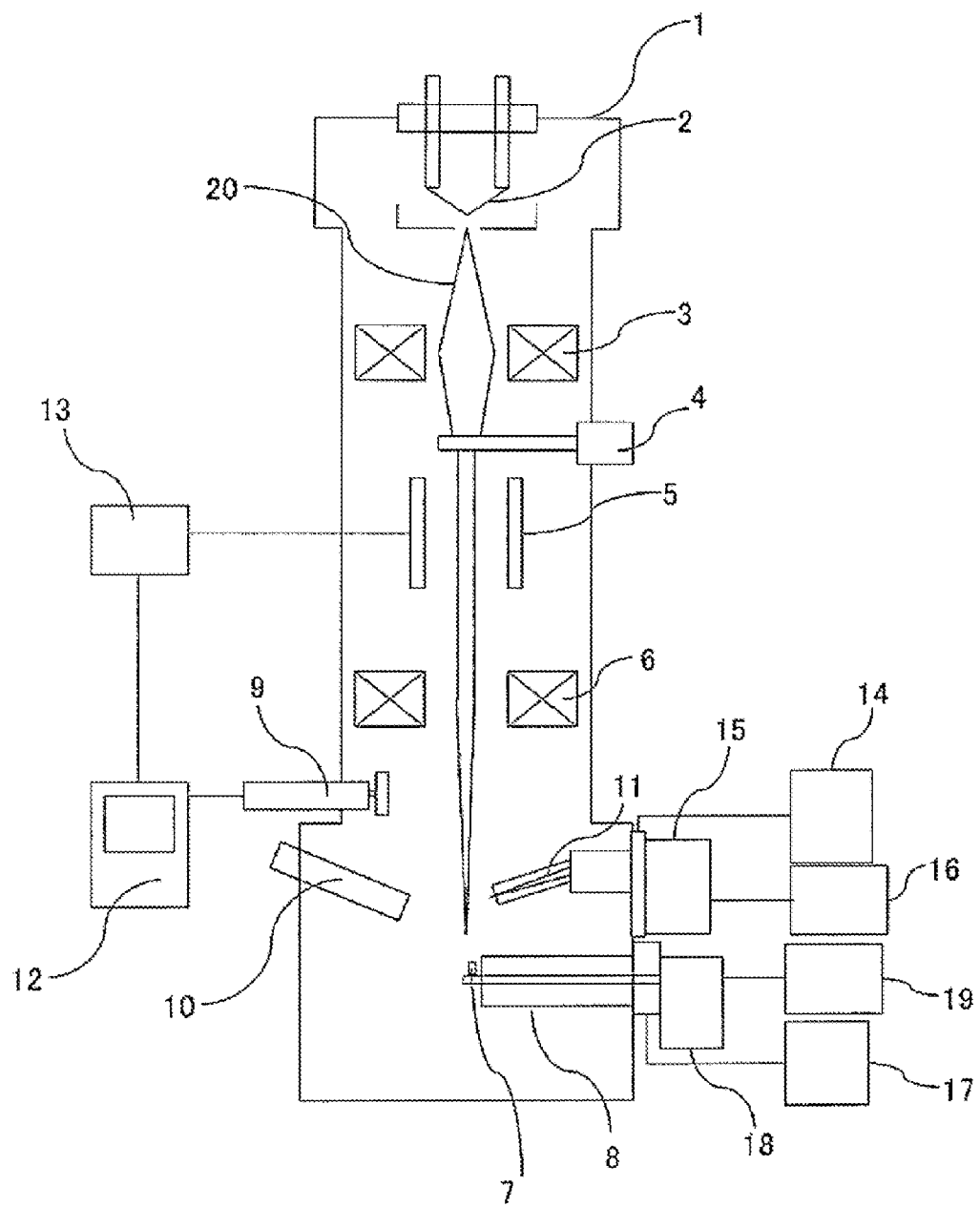
FIG. 1 is a view illustrating a basic constitution of a focused ion beam processing device.

In the present embodiment, a FIB device that prepares a thin film sample from a cooled or frozen sample, a sample holder that retains a cooled state, and a method for preparing a thin film sample from a sample will be explained. FIG. 1 is a constitutional view of a FIB device 1. A mirror body of the FIB device 1 is constituted by an ion source 2, a condenser lens 3, a diaphragm 4, a scanning electrode 5, and an objective lens 6. In a sample chamber of the FIB device 1, a secondary electron detector 9 is attached above a sample holder 8 to which a sample 7 is attached, and a cold trap 10 for preventing contamination such as frost adherence on the sample 7 and a microprobe 11 for conveying a micro sample piece prepared by FIB processing are also attached. The microprobe 11 can be also introduced into another charged particle beam device other than a FIB device. A scanning image display device 12 is connected to the secondary electron detector 9. The scanning image display device 12 is connected to the scanning electrode 5 via a scanning electrode control part 13. An ion beam 20 is emitted from the ion source 2 and is irradiated on the sample 7.

A microprobe control device 14 for position control is connected to the microprobe 11. The microprobe 11 is connected via an internal thermal conduction rod with a microprobe cooling source container 15 that accommodates a cooling source such as liquid nitrogen or liquid helium. A distal end of the microprobe 11 is maintained at an arbitrary temperature by a heater connected to a microprobe temperature adjustment device 16. The microprobe cooling source container 15 is attached to a rear end of the microprobe 11, and the microprobe 11 is integral with the microprobe cooling source container 15 from the distal end of the microprobe 11 up to the microprobe cooling source container 15. Thereby, the microprobe 11 can be removed from the FIB device while maintained in a cooled state. The microprobe cooling source container 15 can also be removed from the microprobe 11.

A sample holder control device 17 for position control is connected to the sample holder 8. The sample holder 8 is connected via an internal thermal conduction rod with a sample holder cooling source container 18 that accommodates a cooling source. A sample fixing part is maintained at an arbitrary temperature by a heater connected to a sample holder temperature adjustment device 19. The sample holder cooling source container 18 is attached to a rear end of the sample holder 8, and the sample holder 8 is integral with the sample holder cooling source container 18 from the sample holder 8 up to the sample holder cooling source container 18. Thereby, the sample holder 8 can be removed from the FIB device while maintained in a cooled state. The sample holder cooling source container 18 can also be removed from the sample holder 8.

FIGS. 2(a) to 2(d) are constitutional views of a distal end portion of the sample holder 8. The sample holder 8 includes a bulk sample holder 8a (FIG. 2(a)) that can fix a bulk sample that has been subjected to a pretreatment such as a quick freezing method while maintaining the bulk sample in a cooled state, and a thin film sample holder 8b (FIG. 2(c)) that can maintain a thin film sample in a cooled state. In the sample holder 8a and the thin film sample holder 8b, a thermal conduction rod 201 that is connected at one end to the sample holder cooling source container 18 (refer to FIG. 1) is connected to a sample fixing part 202 and a mesh sample table 203 respectively, and the sample 7 and a thin film sample 204 are cooled. Further, the sample holder 8a and the thin film sample holder 8b can be maintained at an arbitrary temperature by a heater 205 connected to the sample holder temperature adjustment device 19 (refer to FIG. 1).

The sample holder 8a and the thin film sample holder 8b have sample holder outside cover 206 for preventing frost adherence when transporting a cooled sample in a state in which it is kept on the holder to another device. The sample holder outside cover 206 can move horizontally along a top surface of the sample holders 8a and 8b, and can switch between exposure and non-exposure of the sample fixing part 202 and the mesh sample table 203 to the external atmosphere by the above-mentioned horizontal movement. A state in which the sample holder outside cover 206 is pulled out to a maximum degree in a distal end direction is a closed state, and a state in which the sample holder outside cover 206 is pulled back in a base direction is an opened state. In the closed state of the sample holder outside cover 206, the distal end portion thereof fits closely with an O-ring 207, and thus the inside of the sample holder can be maintained at a specific gas atmosphere. The sample holder control device 17 (refer to FIG. 1) for position control is connected to the sample holder 8a and the thin film sample holder 8b.

Next, a method for extracting an arbitrary position on a frozen sample using the FIB device illustrated in FIG. 1 and the sample holders illustrated in FIGS. 2(a) to 2(d) will be explained referring to the operation explanatory views shown in FIGS. 3(a) to 3(f).

Figure 3A:
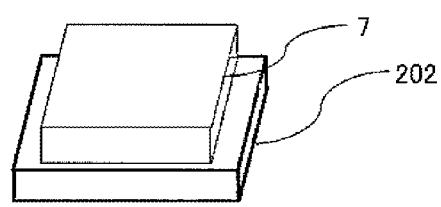
FIGS. 3A to 3H are views explaining a method for preparing a thin film with a microprobe.
Figure 3B:
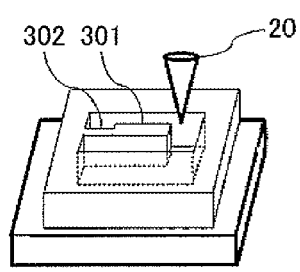
Figure 3C:
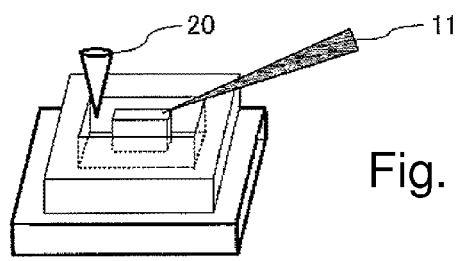
Figure 3D:
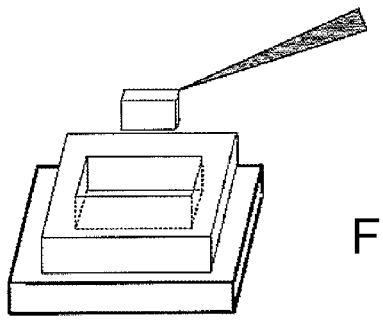
Figure 3E:
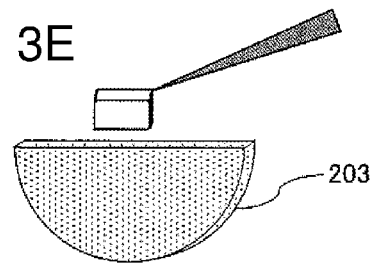
Figure 3F:
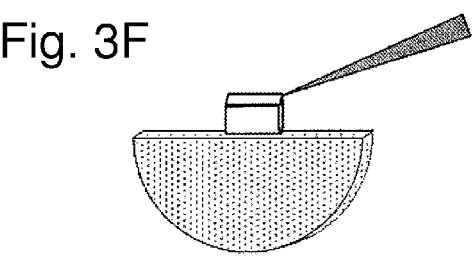
Figure 3G:
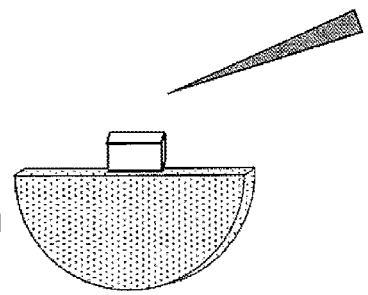
Figure 3H:
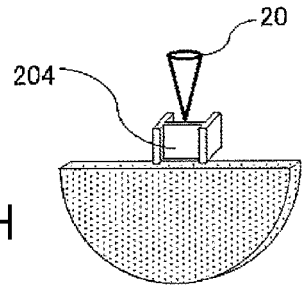

For example, a water-containing sample or a liquid sample is frozen by a pretreatment, and then fixed to the sample fixing part 202 of the sample holder 8a. The sample holder 8a has been precooled by the cooling source in the cooling source container 18. At this time, water vapor in the external air becomes frost and adheres to the surface of the frozen sample. In order to prevent this, after the frozen sample 7 is fixed, the outside cover 206 is quickly closed (FIG. 2(b)) and introduced into the FIB device 1. The sample holder 8a is moved while irradiating the ion beam 20, and a portion to be observed is brought to the center of the field of view (FIG. 3(a)). The surroundings of a bulk-shaped part 301 are sputtered and dug down by the ion beam 20 leaving the bulk-shaped part 301 including a desired observation position and a support part 302 that connects the bulk-shaped part 301 with the periphery (FIG. 3(b)). The microprobe 11 is adhered to the surface of the remaining bulk-shaped part 301 and the sample surface on the periphery of the distal end of the microprobe 11 is sputtered to fix the bulk-shaped part 301 and the microprobe 11 to each other and cut away the support part 302 (FIG. 3(c). The microprobe 11 fixed to the surface of the bulk-shaped part 301 that has been cut out is then raised to extract the bulk-shaped part 301 (FIG. 3(d)). At this time, the bulk-shaped part 301 is maintained in a cooled state by the microprobe 11. While the microprobe 11 is raised up, the sample holder 8a is removed from the FIB device 1, and in exchange, the thin film sample holder 8b is introduced into the FIB device 1. The bulk-shaped part 301 is fixed to the mesh sample table 203 for thin film processing on the thin film sample holder 8b by sputtering the sample table itself (FIG. 3(f)). The microprobe 11 fixed to the surface of the bulk-shaped part 301 is then cut away (FIG. 3(g)). The sample holder 8b on which the mesh sample table 203 is placed has been precooled. Finally, the ion beam 20 is irradiated on the bulk-shaped part 301 on the mesh sample table 203 to sputter it and form a thin film (FIG. 3(h)).

Figure 2A:
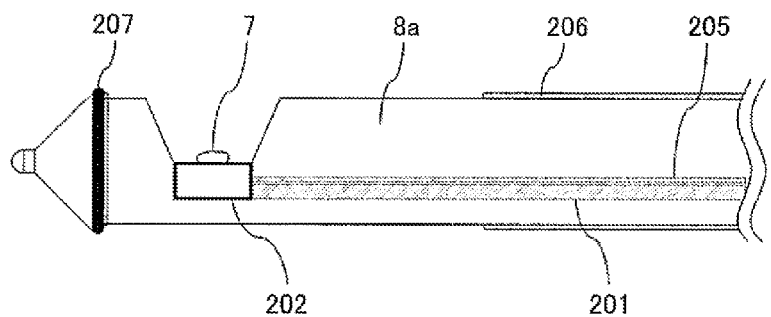
FIGS. 2A to 2D are views illustrating a basic constitutional example of a sample holder.
Figure 2B:
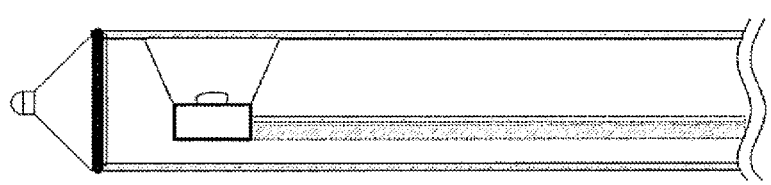
Figure 2C:
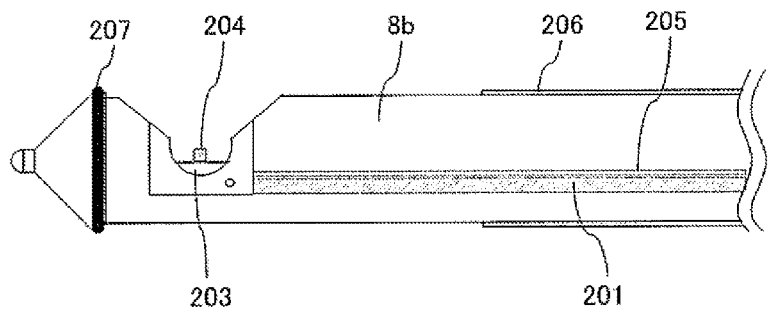
Figure 2D:
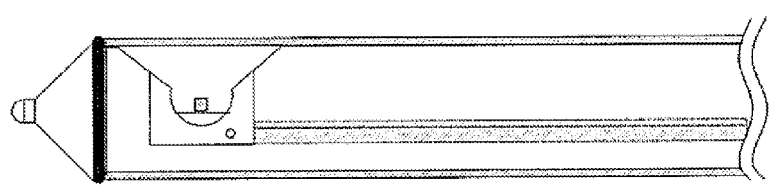

In the case of observing the thin film sample 204 that has been sufficiently thinned, the outside cover 206 of the thin film sample holder 8b is closed (FIG. 2(d)), and the thin film sample holder 8b is removed from the FIB device 1 and transported to a TEM device or STEM device to perform observation. After observation, if it is necessary to make an even thinner sample, the sample holder outside cover 206 is closed within the TEM or STEM device and then the thin film sample holder 8b is removed and transported to the FIB device 1. Therein, the outside cover 206 is opened and additional thin film processing is performed.

Embodiment 2

Figure 4A:
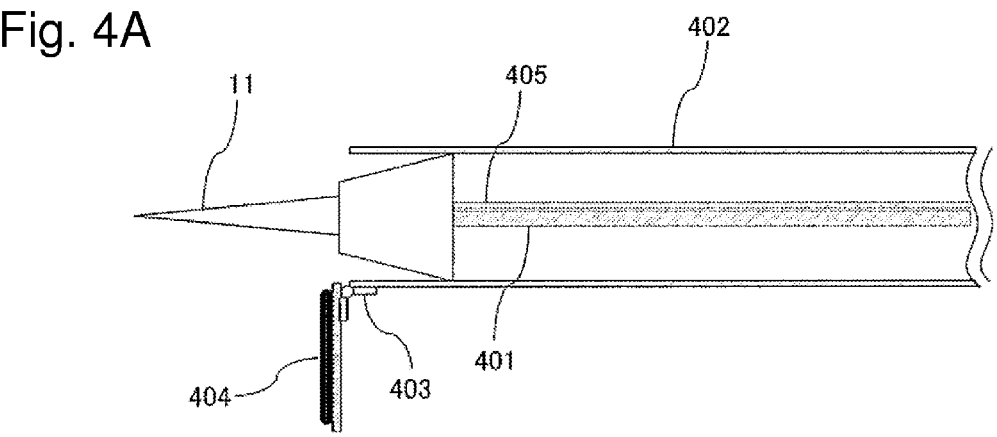
FIGS. 4A and 4B are views illustrating a basic constitutional example of the microprobe.
Figure 4B:
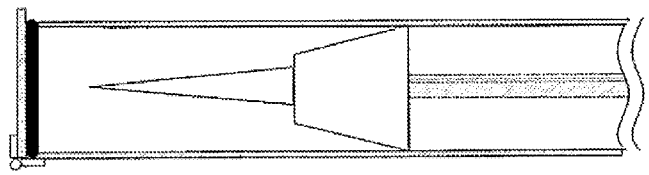

FIGS. 4(a) and 4(b) are constitutional views of the microprobe 11. One end of the microprobe 11 has the probe control device 14 (refer to FIG. 1) and the temperature adjustment device 16 (refer to FIG. 1). The microprobe 11 includes therein a microprobe thermal conduction rod 401 that is connected at one end to the microprobe cooling source container 15 (refer to FIG. 1), and is configured such that the cooling source temperature is transmitted up to the distal end of the microprobe. The microprobe cooling source container 15 and the microprobe distal end side are integrated, and thus can be easily attached/detached in a charged particle beam device and introduced into another charged particle beam device.

FIG. 4(a) illustrates a usage embodiment in a state in which the microprobe 11 is mounted on the FIB device 1. When removing the microprobe 11 to the outside of the FIB device 1 for transport, an external cover 402 is closed before transport in order to prevent water vapor in the atmosphere from becoming frost and adhering to the cooled microprobe 11. When the microprobe outside cover 402 is closed, an opening/closing mechanism 403 also operates in conjunction therewith, and a lid 404 including an O-ring closes (FIG. 4(b)). Thereby, the inside of the microprobe 11 can be retained at a specific gas atmosphere. For example, when the microprobe outside cover 402 is closed within a vacuum of a charged particle beam device, a vacuum degree equivalent to the vacuum degree inside the charged particle beam device can be maintained on the outside of the device as well.

The microprobe temperature adjustment device 16 is connected to a microprobe heater 405 fixed to the distal end portion of the microprobe 11, and can retain the cooling temperature of the microprobe 11 at a temperature set in the microprobe temperature adjustment device 16 or heat the microprobe 11.

Embodiment 3

Figure 5A:
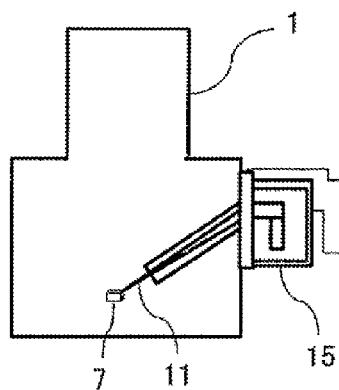
FIGS. 5A to 5E are views explaining a procedure for transporting the microprobe.
Figure 5D:
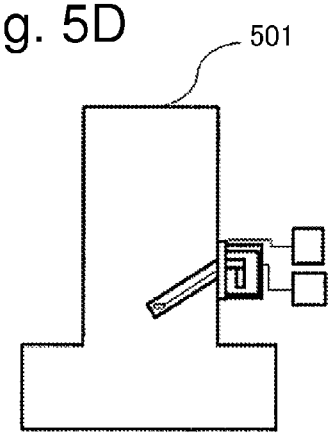
Figure 5B:
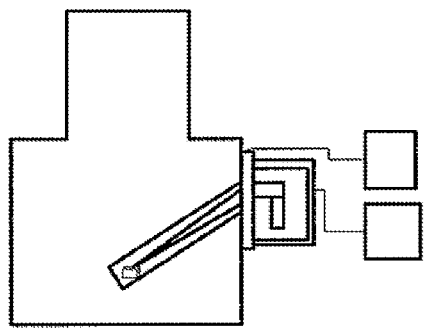
Figure 5E:
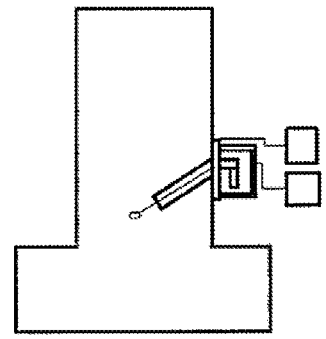
Figure 5C:
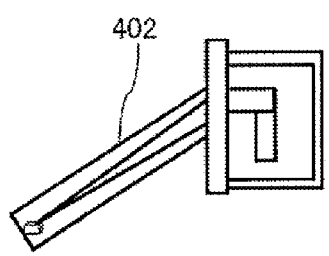

FIGS. 5(a) to 5(e) illustrate the steps of a transport process of the microprobe 11. FIG. 5(a) shows a state in which the sample 7 of an appropriate size has been cut away from a cooled base material sample in the FIB device 1, fixed to the microprobe 11, and extracted. The extracted sample 7 is in a cooled state by thermal conduction from the cooling source on the rear end of the microprobe 11. The extracted sample 7 can be retained at a vacuum degree equivalent to the vacuum degree inside the FIB device 1 due to the mechanism in which the sample 7 can be accommodated inside the microprobe outside cover 402 in the vacuum space of the FIB device 1 (FIG. 5(b)). In a state in which the microprobe 11 is accommodated inside the microprobe outside cover 402, the microprobe 11 is removed from the FIB device 1 to the outside of the device (FIG. 5(c)). At this time as well, the inside of the microprobe outside cover 402 is maintained at the vacuum degree of the FIB device 1, and the sample 7 is in a cooled state.

Next, the microprobe 11 is introduced into a charged particle beam device 501 such as a TEM device or a STEM device. The microprobe 11 is introduced into the vacuum portion of the charged particle beam device 501 (FIG. 5(d)). In a state in which the vacuum of the device has become sufficient, the distal end portion of the microprobe 11 is projected out from the microprobe outside cover 402, and thereby the sample can be observed in the charged particle beam device 501 (FIG. 5(e)).

Embodiment 4

Figure 6A:
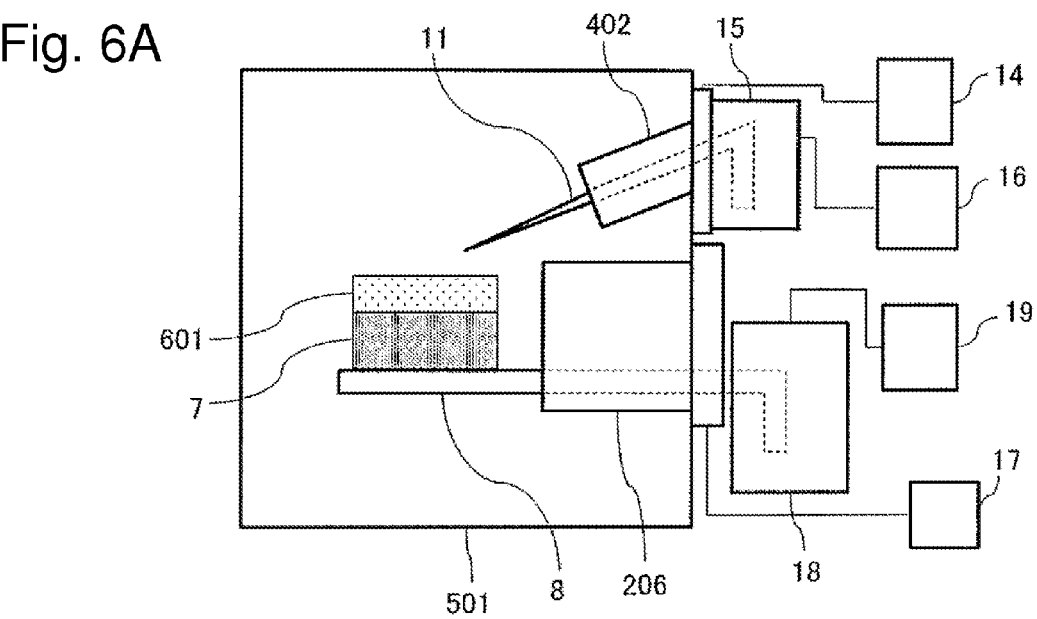
FIGS. 6A and 6B are views explaining a procedure for removing frost on a sample with the microprobe.
Figure 6B:
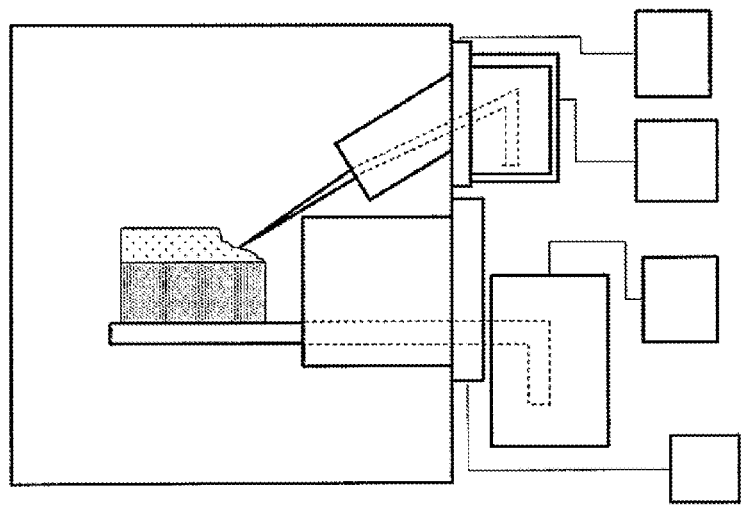
Figure 7A:
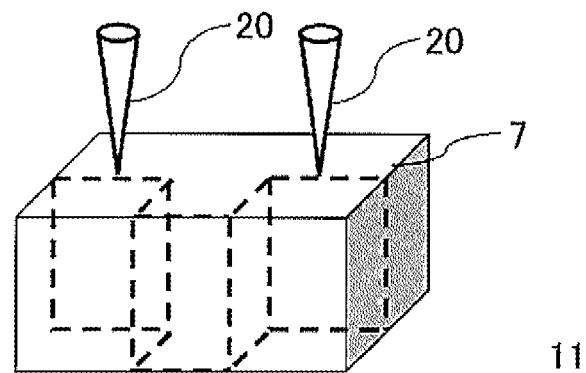
FIGS. 7A to 7D are views explaining a procedure for preparing a frozen cut cross section with the microprobe.
Figure 7B:
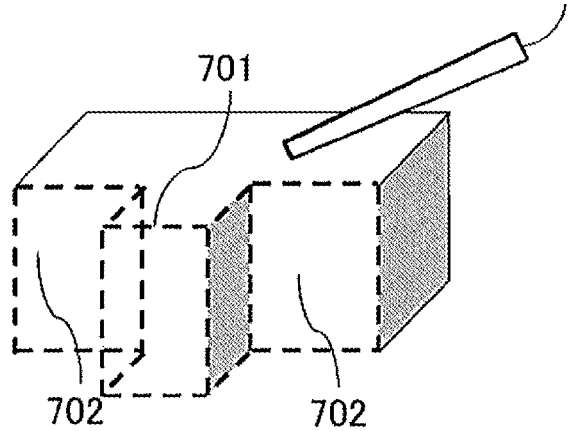
Figure 7C:
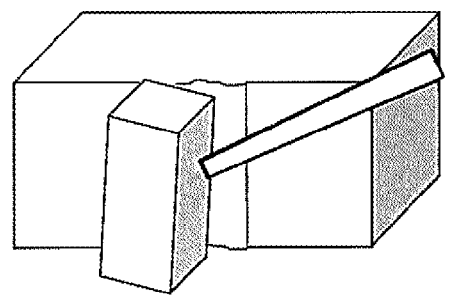
Figure 7D:
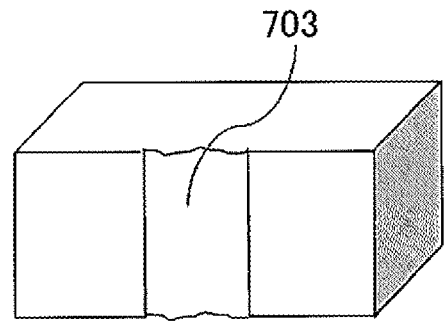

FIGS. 6(a) and 6(b) illustrate the steps for removing frost with the microprobe 11. Since water vapor also exists in the vacuum portion of the FIB device 1 and the other charged particle beam device 501, frost may adhere thickly on the surface of the sample 7 after the cooled sample holder 8 has been introduced. Thus, the microprobe 11 is set and maintained by the microprobe temperature adjustment device 16 at a higher temperature than the sample temperature, such as the frost sublimation temperature. The microprobe 11 that is maintained at an arbitrary temperature is operated to bring it close to the sample surface and contact it to frost 601 on the top thereof (FIG. 6(a)). The frost 601 that has been contacted by the microprobe 11 sublimes due to the contact with the microprobe 11 which has been set to a higher temperature than the sample temperature, and thus the frost can be removed (FIG. 6(b)).

Embodiment 5

FIGS. 7(a) to 7(d) explain a method for preparing a cut cross section of a frozen sample using the microprobe 11. A liquid sample, a biological sample, a polymer material, or the like is frozen using a pretreatment such as a quick freezing method and then fixed to the sample holder 8. The sample holder outside cover 206 is closed so that frost does not adhere to the surface of the sample 7, and then the sample holder 8 is transported to the FIB device 1. After introducing the sample 7 into the FIB device, the sample holder outside cover 206 is opened, and the ion beam 20 is irradiated on the frozen sample to process the frozen sample such that a portion of the sample becomes a convex-shaped part 701 (FIGS. 7(a) and 7(b)). When the microprobe 11 that has been cooled to the same temperature as the frozen sample is operated to push the convex-shaped part 701 from the side surface thereof, the convex-shaped part 701 is broken off (FIG. 7(c)), and a frozen cut cross section 703 that differs from a FIB processed cross section 702 appears (FIG. 7(d)). By this method, the frozen cut cross section 703 and the FIB processed cross section 702 of the sample that has been pretreated can be processed and observed at one time within the FIB device.

Embodiment 6

Figure 8A:
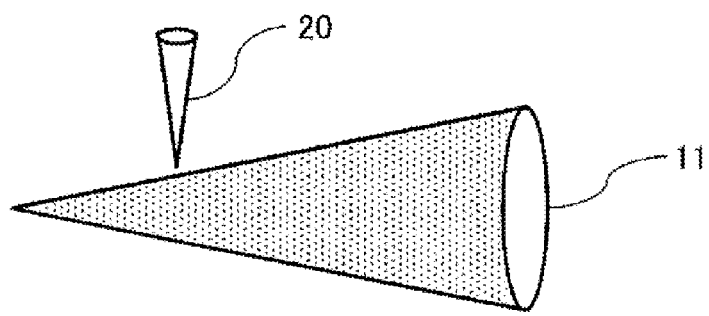
FIGS. 8A to 8D are views explaining a rotation operation of the microprobe, which is one embodiment of the present invention.
Figure 8B:
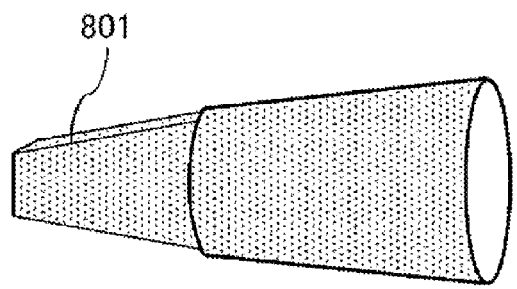
Figure 8C:
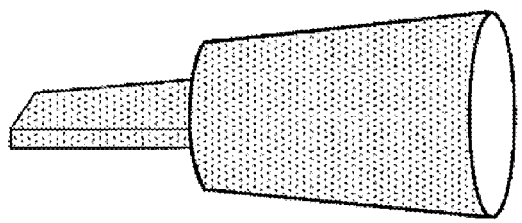
Figure 8D:
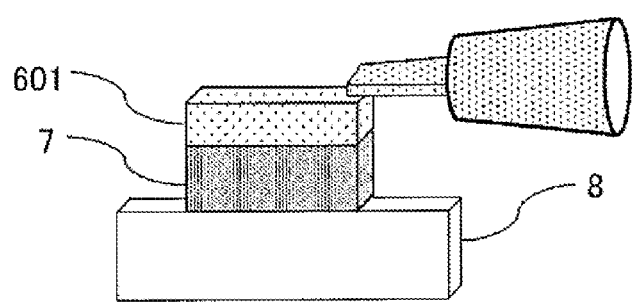

FIGS. 8(a) to 8(d) illustrate the steps of a process for removing the frost 601 by rotating the microprobe 11. The microprobe 11 has a rotation mechanism in the microprobe control device 14. The distal end shape of the probe can be changed according to the use for TEM or STEM observation by FIB processing. For example, as shown in FIG. 8(a), FIB processing is carried out to irradiate the microprobe 11 with the ion beam 20 from above so that the distal end portion of the microprobe 11 becomes a panel-shaped part 801 (FIG. 8(b)). Subsequently, a 90 degree rotation is imparted to the microprobe control device 14, and thereby the panel-shaped part 801 becomes horizontal relative to the surface of the sample 7 (FIG. 8(c)). The microprobe 11 processed in this way is cooled to a slightly higher temperature than the temperature of the cooled sample 7, and then contacted to the frost 601 that has adhered to the surface of the sample 7 (FIG. 8(d)). The microprobe 11 normally has a needle shape, but in the microprobe 11 including a rotation mechanism, the contact surface area with the frost 601 can be increased and the frost can be removed over a wide area by combining the FIB processing and the rotation mechanism.

In the case that the distal end of the microprobe is processed into the panel-shaped part 801 as described above, in order to cool the sample 7 quickly, the microprobe 11 is cooled to near the cooling source temperature and then contacted to the sample surface, and thereby the sample cooling effect can be enhanced.

Embodiment 7

Contaminants near the sample or substances that solidify upon cooling are included inside the vacuum of a charged particle beam device such as a FIB device or a TEM device. When the sample holder 8 on which a cooled sample is mounted is introduced into such a device, contamination or condensation may occur and solidified substances may adhere to the surface of the sample 7 depending on the degree of vacuum within the device or the amount of water vapor included in the vacuum.

In order to prevent this kind of sample contamination, the cold trap 10 is provided in the FIB device 1. However, bringing the microprobe 11 extremely close to the sample 7 and the thin film sample 204 may be difficult considering the size of the cold trap 10.

Thus, for example, the cooling temperature of the microprobe 11 is set to be lower than the cooling temperature of the sample 7 or the thin film sample 204.

Next, by bringing microprobe 11 close to the sample 7 or the thin film sample 204, contaminants near the sample and water vapor is solidified and adsorbed. The diameter of the distal end of the microprobe 11 is on the order of microns, and thus it is possible to bring the microprobe 11 closer to the sample than the cold trap 10.

Embodiment 8

For example, in Embodiment 4, the frost can be removed without any thermal damage to the sample by contacting the microprobe 11, which has been set near the sublimation temperature of the frost, to the frost that has adhered to the surface of the sample. However, thereafter, the degree of vacuum within the device may worsen due to sublimation of the frost.

In this embodiment, a frost removal process and a contaminant adsorption process taking into account the worsening of the degree of vacuum within the charged particle beam device will be explained.

Figure 9:
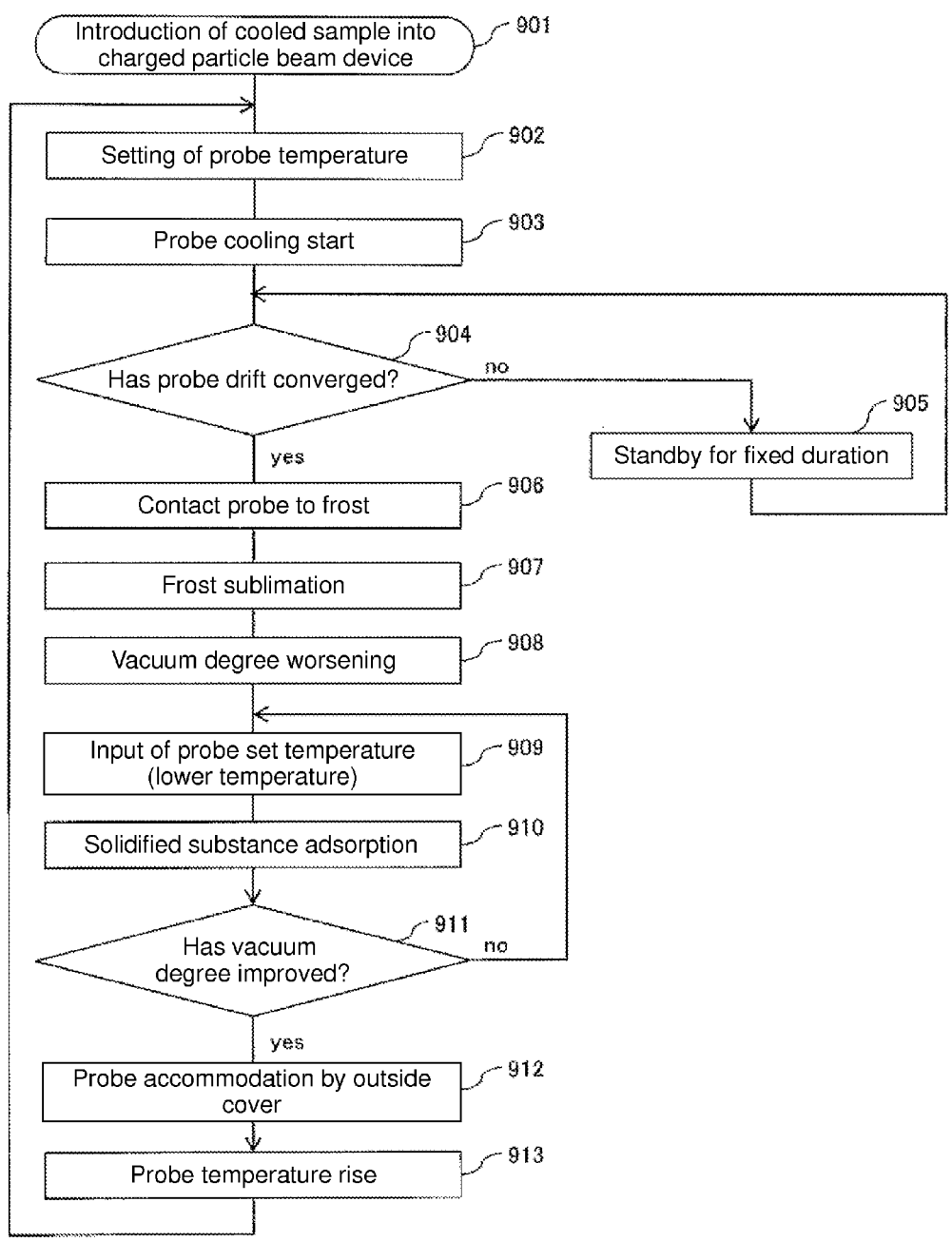
FIG. 9 is a flowchart explaining a frost removal process and a contaminant adsorption process.

FIG. 9 is a flowchart explaining a process for removing frost adhered to the cooled sample and a contaminant adsorption process.

First, the sample holder 8 on which the cooled sample is mounted is introduced into the charged particle beam device (step 901).

Next, the cooling temperature of the microprobe 11 is set higher than the cooling temperature of the sample 7 or the thin film sample 204 (step 902), and then cooling is initiated (step 903).

It is then confirmed whether probe drift has converged (step 904), and if it has not converged, the process enters standby for a fixed duration (step 905). Herein, with regard to the determination of probe drift convergence, the method explained below in Embodiment 12 may also be applied.

Once the drift convergence has been confirmed, next, the microprobe 11 is brought to the vicinity of the sample 7 or the thin film sample 204, and thereby contacted to the frost adhered to the sample (step 906) to sublime the frost (step 907).

Therein, after the frost has been sublimed as described above, the degree of vacuum in the device decreases (step 908). Thus, the set temperature of the microprobe 11 is immediately set to a temperature lower than the sample temperature (step 909), and the microprobe 11 is brought to the vicinity of the sample 7 or the thin film sample 204. Thereby, water vapor released from the sample due to worsening of the degree of vacuum is solidified and adsorbed to the microprobe 11 which is at a lower temperature (step 910).

Therein, it is confirmed whether the degree of vacuum has improved using a vacuum gauge or the like (step 911). Once improvement of the degree of vacuum has been observed, the microprobe 11 is accommodated within the outside cover 402 (step 912). In this state, the set temperature of the microprobe 11 is set at or above the frost sublimation temperature to increase the temperature of the microprobe 11 (step 913), and the adsorbed solidified substances are discharged to the outside of the device. At this time, the gas atmosphere of the microprobe 11 is blocked from the inside of the device by the outside cover 402, and thus degassing of the microprobe 11 can be accomplished without any worsening of the degree of vacuum within the sample chamber in which the sample is placed.

Embodiment 9

A cylindrical tube with a cavity on the inside can also be used as the microprobe 11 described above. In this case, the cooling source within the cooling source container passes through the tube, and then the cooling source is emitted from the distal end of the microprobe, enabling local cooling of the sample.

Therein, the following sequence of steps is executed: an ambient temperature sample is placed on the sample fixing part on an ambient temperature sample holder and then introduced into the FIB device; subsequently, during the actual FIB processing, if it is revealed that the sample is of a type that receives thermal damage by the ion beam irradiation which leads to quality degeneration, the sample holder is removed to the outside of the FIB device, and then the sample is replaced on a sample holder that can be cooled. It takes some time to replace the sample onto the sample holder 8 that can be cooled, and initiate the cooling to reach an optimal cooling temperature for FIB processing.

For example, in a device in which the FIB device 1 is equipped with a microprobe having a cylindrical tube, the sample is fixed to a sample holder at ambient temperature. If cooling of the sample becomes necessary during FIB processing, the cooling source is emitted from the distal end of the microprobe. Thereby, the sample that has contacted the cooling source is cooled locally to near a cooling temperature. When stopping the emission of the cooling source, the orientation of the microprobe is rotated so that the liquid level of the cooling source does not reach higher than a distal end position of the tube.

It is also possible to cool the sample with the cooling source emitted from the microprobe without using the cooling action of the sample holder, and thus the sample can be efficiently cooled without replacing the sample on the sample holder or any waiting time for cooling.

The above-described example can be introduced into not only a FIB device but also a TEM device, a STEM device, a SEM device, and the like, and similar effects can be achieved in such cases.

Embodiment 10

An example of cooling in-situ observation using the microprobe 11 will now be explained. In-situ observation is a method of direct dynamic observation of the process of changes of a sample in a charged particle beam device or the like.

When an ambient temperature sample that has been introduced into a charged particle beam device is contacted with the microprobe 11 that has been set to an arbitrary temperature, the portion of contact is gradually cooled, and the sample approaches the set temperature of the microprobe 11. Structural changes within the sample that accompany this cooling can be continuously observed. For example, the thin film sample 204 at ambient temperature is introduced into a TEM device or a STEM device, and then the microprobe 11 is contacted to the vicinity of the surface of the thin film sample 204. The temperature of the microprobe 11 is set to a temperature at which the structural changes of the sample occur. The sample that has been contacted gradually approaches the set temperature of the microprobe 11 from an ambient temperature state. During this time, continuous observation by a charged particle beam is carried out.

In the thin film sample 204, in addition to observation using a STEM detector, element distribution changes can also be confirmed together with the passage of the cooling time using Electron Energy-Loss Spectroscopy (EELS) or Energy Dispersive X-Ray Spectroscopy (EDX). Further, changes in the crystal grain size or crystal orientation can be analyzed at an arbitrary cooling temperature by Electron Backscatter Diffraction Pattern (EBSP).

Depending on the material properties of the sample, there are cases in which the structural changes exhibit different phenomena depending on whether the sample cools gradually or cools quickly. Thus, a user can select from the two modes of a gradual cooling mode or a quick cooling mode for the cooling speed of the microprobe 11. In a vacuum, thermal conduction to the sample is instantaneous. In the quick cooling mode, the temperature is set lower than the temperature at which the structural changes of the sample occur, and the microprobe 11 set at this temperature is contacted to the vicinity of the sample surface. On the other hand, in the gradual cooling mode, a temperature reducing speed of the microprobe 11 can be set. By setting the range of reduction of the temperature over an arbitrary duration of the microprobe 11 that has been contacted to the vicinity of the sample surface, the sample can be gradually cooled.

Further, when performing cooling in-situ observation, the changes in the sample structure by temperature reduction are continuous, and thus video can be used to record the observation.

Figure 10:
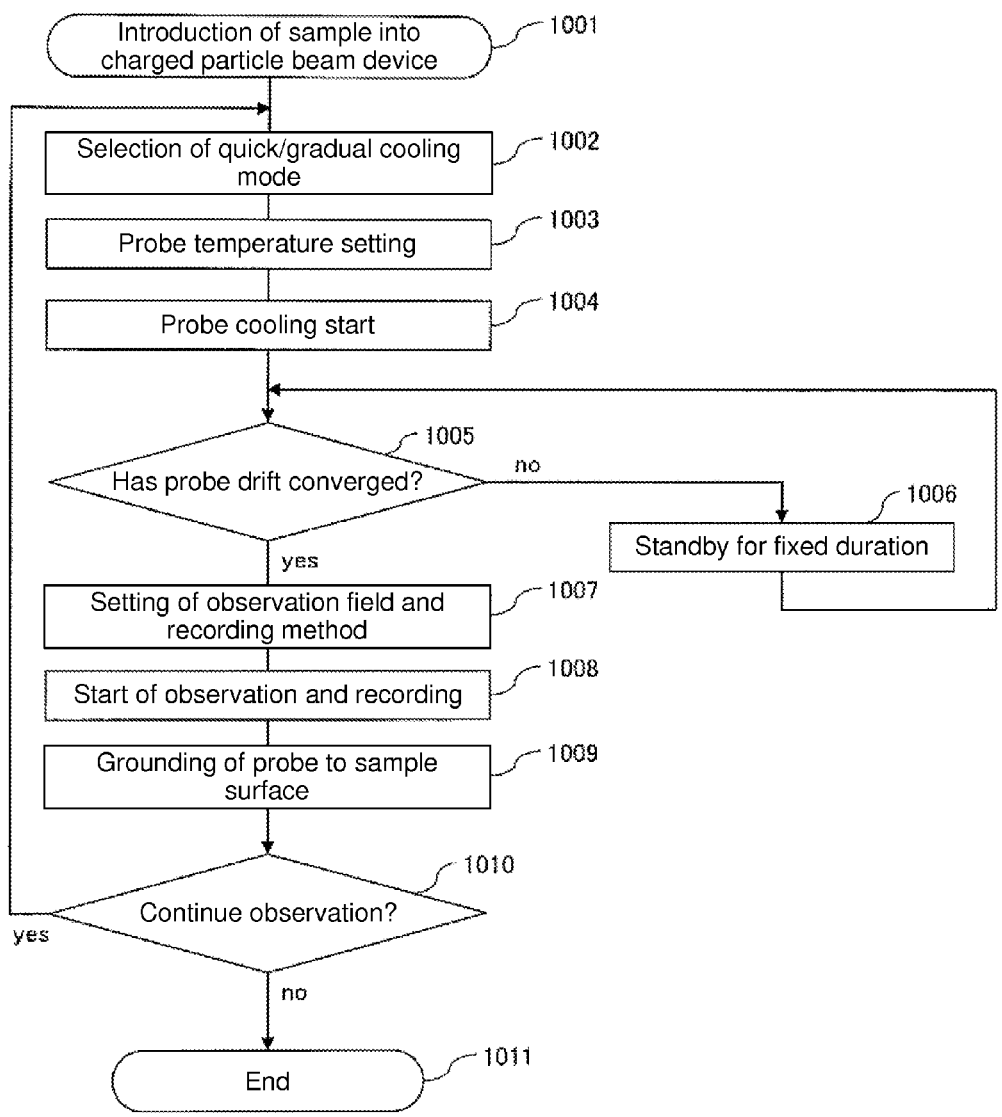
FIG. 10 is a flowchart explaining a cooling in-situ observation (quick cooling mode) process.

FIG. 10 is a flowchart explaining a cooling in-situ observation (quick cooling mode) process. First, an ambient temperature sample is introduced into the charged particle beam device (step 1001), and a quick cooling mode is selected from the cooling modes (quick cooling/gradual cooling modes) (step 1002).

Next, the probe temperature is set (step 1003), and cooling is initiated (step 1004).

It is then confirmed whether probe drift has converged (step 1005), and if it has not converged, the process enters standby for a fixed duration (step 1006). Herein, with regard to the determination of probe drift convergence, the method explained below in Embodiment 12 may also be applied.

Once the drift convergence has been confirmed, next, an observation field and a recording method are set (step 1007), and observation and recording are initiated (step 1008).

Here, the probe is grounded to the surface of the sample to observe the inside of the sample (step 1009). After observation of a predetermined region or for a predetermined duration has been performed, the process returns to step 1002 if further observation is to be carried out (step 1010). Alternatively, the observation is completed here (step 1011).

Figure 11:
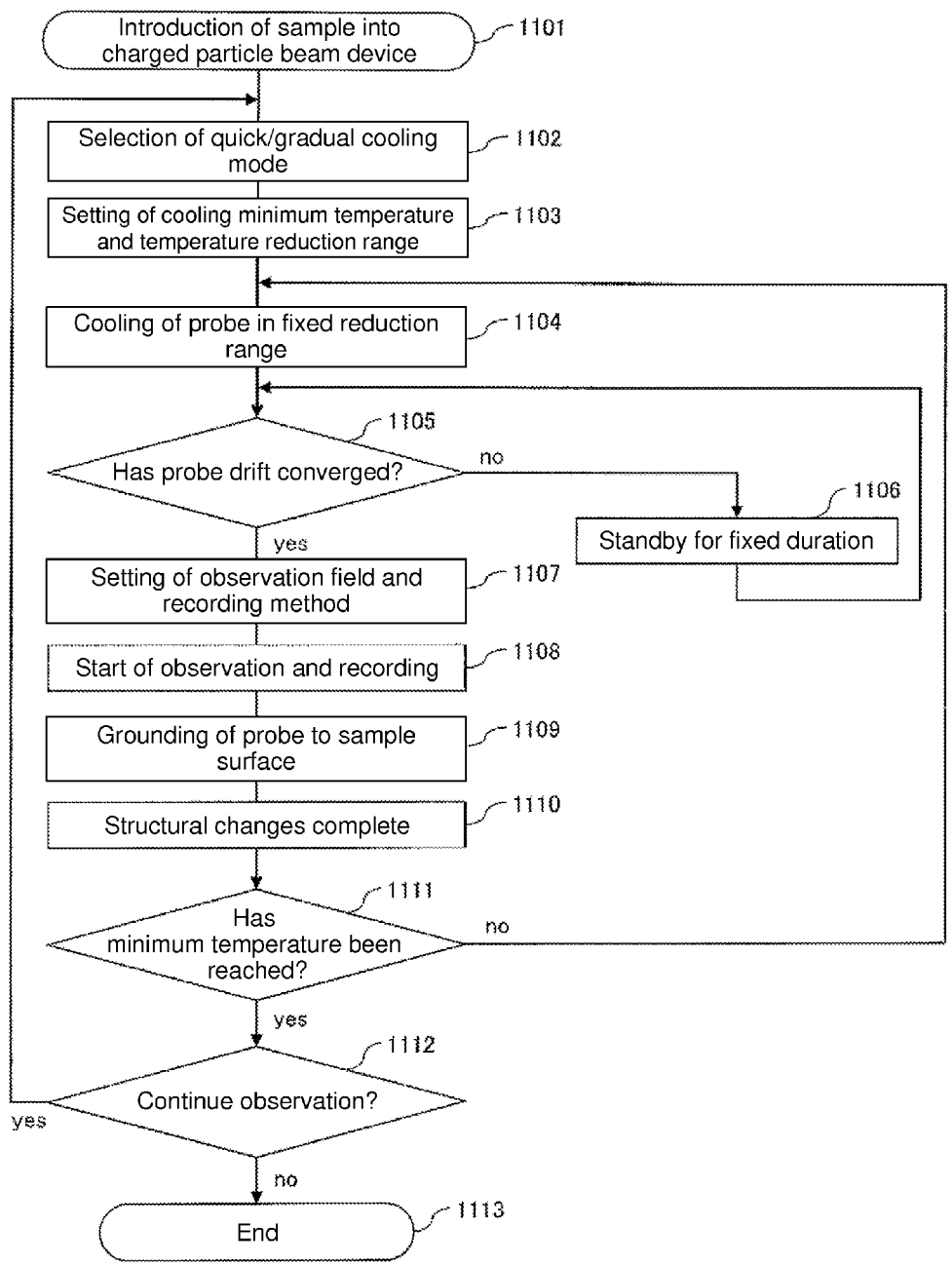
FIG. 11 is a flowchart explaining a cooling in-situ observation (gradual cooling mode) process.

FIG. 11 is a flowchart explaining a cooling in-situ observation (gradual cooling mode) process. First, an ambient temperature sample is introduced into the charged particle beam device (step 1101), and a gradual cooling mode is selected from the cooling modes (quick cooling/gradual cooling modes) (step 1102).

Next, the cooling minimum temperature and temperature reduction range of the probe is set (step 1103), and the probe is cooled in a fixed reduction range (step 1104).

It is then confirmed whether probe drift has converged (step 1105), and if it has not converged, the process enters standby for a fixed duration (step 1106). Herein, with regard to the determination of probe drift convergence, the method explained below in Embodiment 12 may also be applied.

Once the drift convergence has been confirmed, next, an observation field and a recording method are set (step 1107), and observation and recording are initiated (step 1108).

Here, the probe is grounded to the surface of the sample to observe the inside of the sample (step 1109). Once completion of the structural changes inside the sample has been confirmed (step 1110), it is confirmed whether the probe has reached the minimum temperature set in step 1103 (step 1111). If the probe has not reached the minimum temperature that was set, the process returns to step 1104 and cooling is performed again. On the other hand, if the probe has reached the minimum temperature, the process returns to step 1102 if further observation is to be carried out (step 1112). Alternatively, the observation is completed here (step 1113).

Embodiment 11

The microprobe heater 405 is provided within the microprobe 11 for maintaining a set temperature. The sample can be heated using heat generated by the microprobe heater 405. For example, in the case that processing or observation of the cooled sample has completed and the sample is to be removed to the outside of the charged particle beam device, if the sample is removed as is in a cooled state to the atmospheric air, the sample may be contaminated by water vapor or contaminants in the atmospheric air. Therefore, it is necessary to return the sample temperature to room temperature within the charged particle beam device. Therein, the sample can be warmed to room temperature by the heater 205 built into the sample holder 8, but this takes time. Thus, in addition to heating by the heater 205 of the sample holder 8, the microprobe 11 that has been warmed by the microprobe heater 405 of the microprobe can be contacted to the cooled sample to shorten the time for returning the sample to room temperature.

Embodiment 12

When the microprobe 11 is cooled, a phenomenon called thermal drift occurs in which the microprobe 11 continuously moves without stopping at a specific position until it nears the thermal equilibrium of the microprobe set temperature.

Figure 12A:
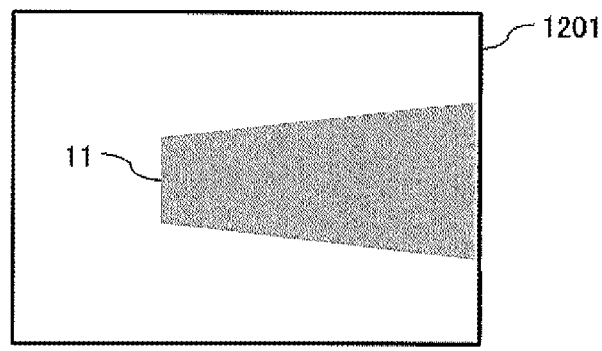
FIGS. 12A to 12C are schematic views illustrating images observing thermal drift during probe cooling.
Figure 12B:
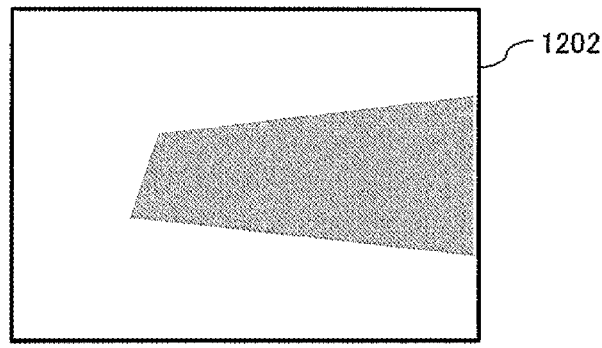
Figure 12C:
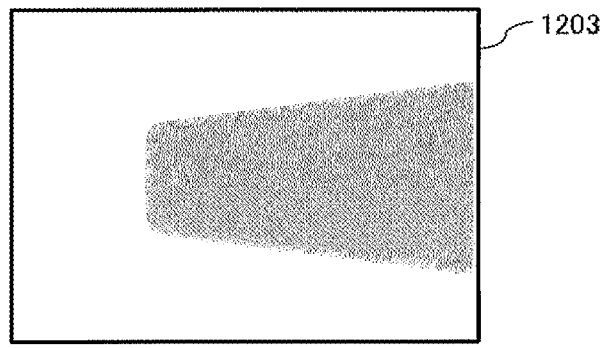

In the present embodiment, a method for correctly determining whether the probe drift has converged will be explained using FIGS. 12 and 13. FIGS. 12(*a*) to 12(*c*) illustrate examples using images of one method for determining the probe drift convergence. In determining whether the microprobe 11 has reached thermal equilibrium and the drift has converged such that the microprobe 11 is in a state in which it can be used safely, the microprobe 11 can be imaged and the obtained images can be used. For example, when the microprobe 11 begins to be cooled by a cooing medium, the microprobe 11 exhibits thermal drift in which it contracts. The direction of movement of the thermal drift is the same as the elongation direction of the microprobe thermal conduction rod 401. Therefore, if the microprobe 11 during thermal drift is imaged by a SEM device or STEM device, an image 1202 is captured in which the microprobe extends diagonally relative to a field of view as shown in FIG. 12(*b*). In a TEM device, since several transmission images are integrated, an image 1203 is captured in which the outline of the microprobe 11 is blurred as shown in FIG. 12(*c*). When the thermal drift has converged, the vertical direction of the microprobe 11 is imaged vertically relative to the field of view.

Utilizing this phenomenon, an image 1201 of the microprobe 11 before cooling has started is compared with the image 1202 or the image 1203 of the microprobe 11 imaged at a fixed interval from the start of cooling, and thereby is it determined whether the microprobe 11 has reached thermal equilibrium of the set cooling temperature and stabilized. During imaging, in SEM or STEM, a method called SLOW SCAN is used, in which the speed of scanning the electron beam is set to scan over several tens of seconds. For example, by pushing a thermal drift convergence determination button displayed on a display device screen or the like simultaneously with the start of cooling, an instruction is transmitted to a control device. A user inputs an arbitrary time width and scanning speed, and after imaging immediately after the start of cooling, a scanning image is obtained over the set time width. During cooling, the vertical end face of the microprobe 11 is displayed as in the image 1202 in which it is elongated diagonally due to thermal drift. When this end face has reached the vertical direction relative to the field of view again, the display of the thermal drift convergence determination button switches, and thus the device user can use the microprobe 11.

Figure 13:
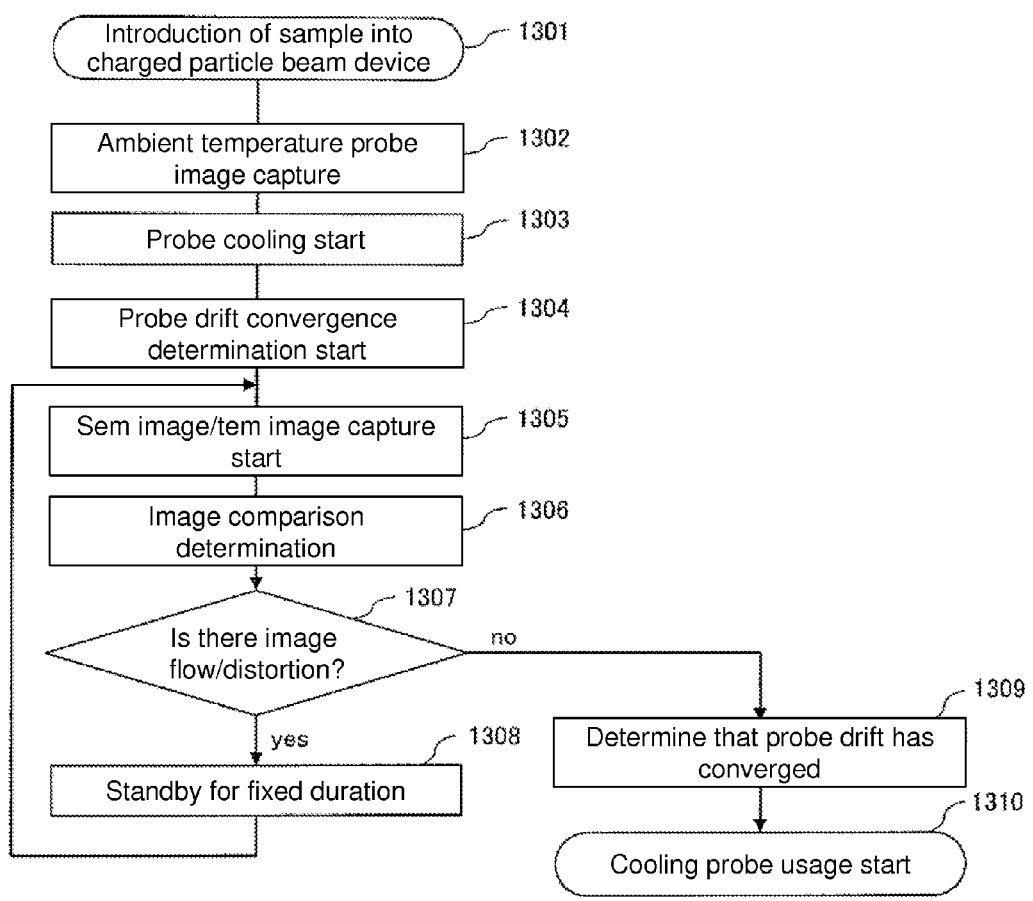
FIG. 13 is a flowchart explaining a thermal drift convergence determination method during probe cooling.

FIG. 13 is a flowchart explaining an operation for determining the probe drift convergence. First, a sample is introduced into the charged particle beam device (step 1301), and an image of the probe is captured in an ambient temperature state (step 1302). Next, the probe is cooled to the preset cooling temperature (step 1303).

Herein, when instructed to start the process for determining whether the probe drift has converged by, for example, a control device or the like (step 1304), imaging of a SEM image, a STEM image, or a TEM image begins (step 1305).

The images captured before and after the start of cooling as explained above referring to FIGS. 12(a) to 12(c) are compared (step 1306). If there is image flow or distortion (step 1307), the process enters standby for a fixed duration (step 1308).

On the other hand, if it is determined that there is no image flow or distortion, it is determined that the probe drift has converged (step 1309), and use of the cooled probe begins (step 1310).

Embodiment 13

The cooled sample also exhibits the phenomenon called thermal drift in which the cooled sample continuously moves without stopping at a specific position until it nears the thermal equilibrium of the set temperature of the sample holder on which the sample is fixed. Even after reaching the set temperature, it takes some time for the thermal drift to converge. In a method in which the above-described microprobe is set near the sample and used as an anti-contamination trap or a method in which the cooling source is emitted from the cylindrical microprobe onto the sample as described above in Embodiment 8, the position of the microprobe may deviate from the sample that is continuously moving due to thermal drift. Alternatively, sample breakage may occur when the position of the microprobe approaches the sample due to thermal drift, and thus it may become difficult to stably achieve the effects described in the embodiment. Thus, the microprobe control device 14, which functions to control the position of the microprobe 11, has a function to make the microprobe 11 track the sample corresponding to the thermal drift at a target location of processing or observation.

For example, if the sample holder 8 is set to a certain arbitrary temperature, a heater is started or stopped by the temperature adjustment device 19 so that the sample holder 8 approaches the set temperature. Thermal drift occurs simultaneously with the occurrence of a temperature change to the set temperature until thermal equilibrium is reached, and the sample on the sample fixing part 202 or the mesh sample table 203 moves continuously. At this time, the sample is observed in advance at fixed intervals every few seconds to confirm the amount of movement due to thermal drift, and the same amount of movement is input into the microprobe control device 14. Thereby, the microprobe 11 also moves tracking the sample 7 or the thin film sample 204. By repeating the above steps, the microprobe can track the sample, and even if thermal drift occurs, the effects thereof can be mitigated.

Embodiment 14

As another method for the tracking function, in a processing/observation device (FIG. 14) called a FIB-SEM device in which a FIB column and a SEM column are mounted, a SEM column 1402 having an electron gun and a FIB column 1401 having an ion gun are mounted at certain angles. Therefore, the sample or microprobe can be observed from different directions. Therein, a SEM image can be obtained by detecting a secondary electron 1403 emitted from the sample. The position of the microprobe and the sample can be maintained at a fixed position three-dimensionally by the two types of images obtained by FIB and SEM.

Figure 14:
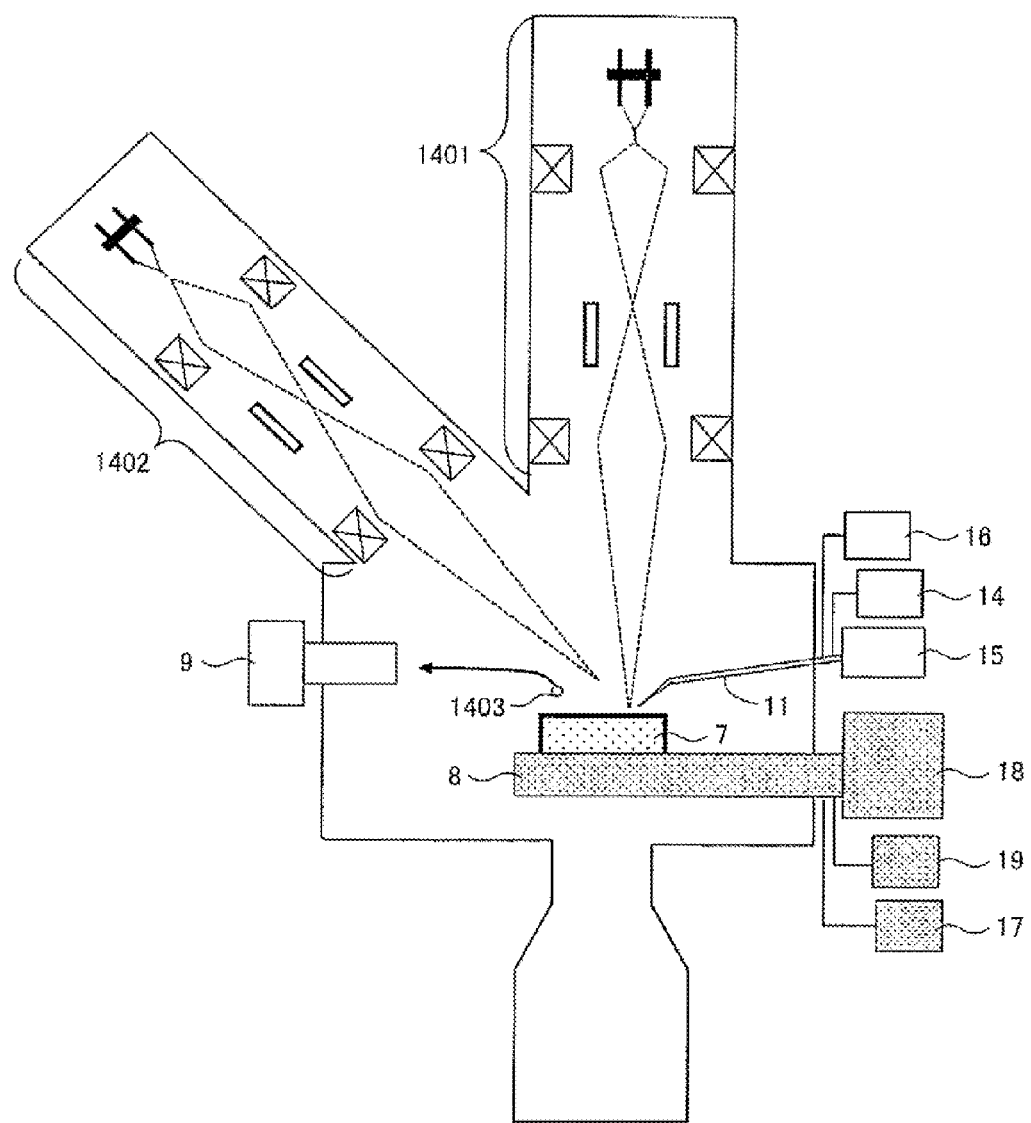
FIG. 14 is a view illustrating a basic constitution of a focused ion beam and an electron beam processing observation device.

In FIG. 14, the FIB column is mounted vertically, and the SEM column is mounted at a position that is tilted toward the horizontal direction relative to the FIB column. In the SEM image, movement of the sample in the Z direction (height) and X direction can be confirmed. In the FIB image, since the ion beam is irradiated onto the sample from directly above, movement of the sample in the X direction and the Y direction can be confirmed.

Figure 15:
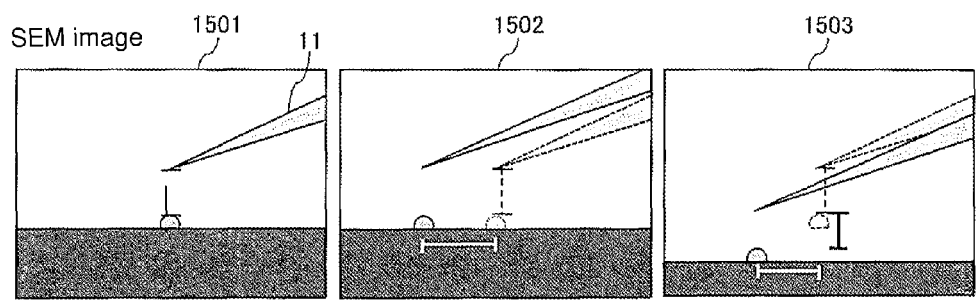
FIG. 15 is a view explaining a probe tracking function using images, which is one embodiment of the present invention.
Figure 15:
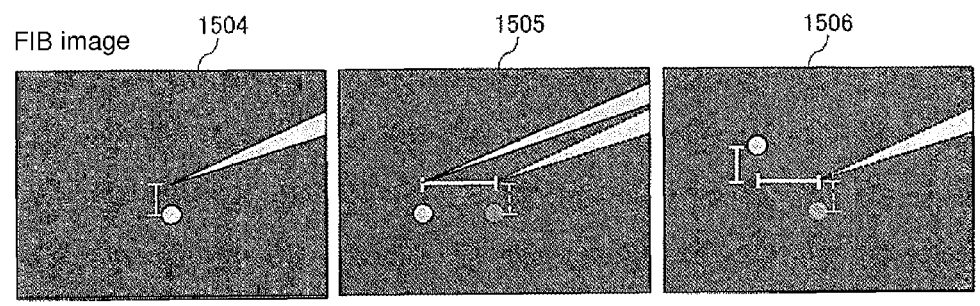

FIG. 15 explains the microprobe tracking using the SEM images and the FIB images.

First, the microprobe 11 is set near an arbitrary position of the cooled sample. At this time, a SEM image 1501 and a FIB image 1504 are captured so that the arbitrary position of the sample and, for example, the distal end of the microprobe 11 are in the field of view. In the captured SEM image 1501 and FIB image 1504, the distance between the two points of a point at the distal end of the microprobe 11 and a point on the sample is measured. Using this measured distance as an initial value, the probe and the sample can be mutually tracked so as to maintain the distance between the probe and the sample at the initial value.

When the microprobe 11 or the sample holder 8 is subjected to a temperature change, the microprobe 11 or the sample holder 8 that has been subjected to a temperature change begins moving in a fixed direction due to thermal drift. In the SEM image, the amount of movement in the X direction and the Z direction can be measured. In a SEM image 1502 captured after the microprobe 11 or the sample holder 8 has been subjected to a temperature change, drift in the X direction of the sample 7 or the microprobe 11 is observed. If the distal end of the microprobe 11 and the point on the sample separate from each other, the distance at this time is measured, a movement amount for returning to the initial value is calculated, and this movement amount is input to the sample holder 8 or the microprobe 11. At this time, drift in the X direction can also be recognized in a FIB image 1505 captured by FIB. In the FIB image, the amount of movement in the X direction and the Y direction can be measured. Similarly, in the FIB image, if the distal end of the microprobe 11 and the point on the sample separate from each other, this distance is measured, a movement amount for returning to the initial value is calculated, and this movement amount is input to the sample holder 8 or the microprobe 11.

Next, in a SEM image 1503 and a FIB image 1506 captured in order, drift in the Z direction and the X direction of the sample or the microprobe 11 is confirmed in the SEM image 1503, and the amount of movement from the initial value is calculated. In the FIB image 1506, drift in the X direction and Y direction is confirmed, and the amount of movement from the initial value is calculated. These movement amounts are input to the sample holder 8 or the microprobe 11, and thereby the distance between the microprobe 11 and the sample is maintained at the initial value.

Since the FIB images and the SEM images are captured and acquired alternately, the movement amount in the X direction is input at the time of acquiring either one of the SEM image or the FIB image. Thus, the movement amount in the X direction which can be confirmed in the FIB image and the SEM image is not duplicated. The SEM image and the acquisition of an SIM image is conducted over a time width set by the user. When the amount of movement has reached zero, the tracking is no longer necessary because the microprobe 11 or the sample holder 8 has reached thermal equilibrium. Thereafter, if the cooling source within the cooling source container of the microprobe 11 or the sample holder 8 has become depleted, the temperature begins to rise, and the distance between the two points of a point at the distal end of the microprobe 11 and a point on the sample changes again from the initial value due to thermal drift. In this case as well, the amount of movement is calculated from the distance between the two points and then input.

By the above-described function, tracking relative to the thermal drift can be carried out over a long period of time. Further, since the distance between the two points can be measured from the X, Y, and Z directions, the risk of sample breakage or the like due to collision of the microprobe 11 or the sample 7 can be prevented, and thus more stable tracking can be executed.

REFERENCE SIGNS LIST

1 FIB device
2 ion beam
3 condenser lens
4 diaphragm
5 scanning electrode
6 objective lens
7 sample
8 sample holder
8a sample holder
8b thin film sample holder
9 secondary electron detector
10 cold trap
11 microprobe
12 scanning image display device
13 scanning electrode control part
14 microprobe control device
15 microprobe cooling source container
16 microprobe temperature adjustment device
17 sample holder control device
18 sample holder cooling source container
19 sample holder temperature adjustment device
20 ion beam
201 thermal conduction rod
202 sample fixing part
203 mesh sample table
204 thin film sample
205 heater
206 sample holder outside cover
207 O-ring
301 bulk-shaped part
302 support part
401 microprobe thermal conduction rod
402 microprobe outside cover
403 opening/closing mechanism
404 lid
405 microprobe heater
501 charged particle beam device
601 frost
701 convex-shaped part
702 FIB processed cross section
703 frozen cut cross section
801 panel-shaped part
1201 ambient temperature microprobe observation image
1202 integrated observation image of microprobe after cooling start
1203 slow scan observation image of microprobe after cooling start
1401 FIB column
1402 SEM column
1403 secondary electron
1501 SEM image at time of initial value measurement
1502 SEM image at time of X direction movement
1503 SEM image at time of X and Z direction movement
1504 FIB image at time of initial value measurement
1505 FIB image at time of X direction movement
1506 SEM image at time of X and Y direction movement

The invention claimed is:

1. A method of preparing a sample using a charged particle beam device comprising a microprobe having a cooling mechanism, a first sample holder having a mechanism for retaining a sample in a cooled state, and a stage into which the microprobe and the first sample holder can be introduced, the method comprising:
    cutting a bulk-shaped sample piece from the sample on the first sample holder retained in a cooled state;
    adhering the sample piece to a distal end of the microprobe that is cooled to a fixed temperature and transferring the sample piece to a second sample holder for thin film observation retained in a cooled state, which is different from the first sample holder, within a vacuum chamber of the charged particle beam device;
    separating the sample piece that has been transferred to the second sample holder from the microprobe and thin film processing the sample piece to a thickness that is less than the thickness during cutting; and
    observing the sample piece after the thin film processing.

2. The method of preparing a sample according to claim 1, further comprising contacting the microprobe that has been temperature controlled to a temperature higher than a sublimation temperature of a thin film deposited on a surface of the sample on the first sample holder to the surface of the sample to sublime and remove the thin film on the surface of the sample.

3. The method of preparing a sample according to claim 1, further comprising bringing the microprobe that has been temperature controlled to a temperature equal to or less than a temperature of the sample on the first sample holder close to the sample to adsorb contaminant components in a vacuum within the charged particle beam device.

4. The method of preparing a sample according to claim 1, further comprising changing a temperature of the sample by contacting the microprobe that has been temperature controlled to the surface of the sample mounted on the first sample holder.

5. The method of preparing a sample according to claim 1, further comprising:
contacting the microprobe to the sample at ambient temperature retained on the second sample holder;
cooling the microprobe by a cooling source container connected to the microprobe; and
continuously observing changes that occur when the sample is cooled.

6. The method of preparing a sample according to claim 1, further comprising:
selecting a cooling speed for the microprobe and cooling the microprobe at the selected cooling speed by the cooling source container connected to the microprobe;
contacting the microprobe to a surface of the sample at ambient temperature mounted on the first sample holder or to the sample at ambient temperature retained on the second sample holder; and
continuously observing changes that occur when the surface of the sample mounted on the first sample holder or the sample retained on the second sample holder is cooled.

7. The method of preparing a sample according to claim 1, further comprising applying a load with the microprobe that has been temperature controlled to a convex-shaped portion of the sample mounted on the sample holder that is retained in a cooled state to cut a portion of the sample.

8. A charged particle beam device comprising:
a charged particle source that emits charged particles;
a first sample holder having a mechanism for retaining a sample in a cooled state;
a microprobe having a cooling mechanism;
a stage into which the microprobe and the first sample holder can be introduced; and
a control part that controls the following processes:
cutting a bulk-shaped sample piece from the sample on the first sample holder retained in a cooled state;
adhering the sample piece to a distal end of the microprobe that is cooled to a fixed temperature and transferring the sample piece to a second sample holder for thin film observation retained in a cooled state, which is different from the first sample holder, within a vacuum chamber of the charged particle beam device;
separating the sample piece that has been transferred to the second sample holder from the microprobe and thin film processing the sample piece to a thickness that is less than the thickness during cutting; and
observing the sample piece after the thin film processing.

9. The charged particle beam device according to claim 8, wherein the control part measures a position coordinate of the sample on the first sample holder from a microscope image, and displaces a position of a distal end of the microprobe following a displacement of the coordinate of the sample.

10. A sample holder for thin film observation comprising:
a cooling mechanism for retaining a sample in a cooled state; and
a cylindrical cover that slides to an accommodation position and seals so as to block a sample piece adhered to a distal end of a microprobe from a surrounding atmosphere when moving the sample between charged particle beam devices.

11. A microprobe comprising:
a thermal conduction member that is connected at one end to a microprobe main body;
a cooling medium that is connected to the other end of the thermal conduction member;
a cooling source container that retains the cooling medium;
a temperature measurement mechanism connected to the microprobe main body; and
a temperature control circuit connected to the temperature measurement mechanism;
wherein the thermal conduction member is also connected to a heating medium that is a heater capable of heat control using an electrical means;
wherein the temperature control circuit controls the heating of the heater to control a temperature; and
wherein the microprobe can be removed from a vacuum chamber of a charged particle beam device in a state in which the connections of the thermal conduction member, the cooling medium, the heating medium, and the temperature measurement mechanism are maintained.

12. The microprobe according to claim 11, wherein the microprobe further comprises:
a cylindrical cover that slides to an accommodation position to accommodate a distal end of the microprobe when moving the microprobe between charged particle beam devices; and
a lid that closes a distal end part of the cylindrical cover that has slid to the accommodation position and seals so as to block a sample piece adhered to the distal end of the microprobe from a surrounding atmosphere.

13. A microprobe comprising:
a thermal conduction member that is connected at one end to a microprobe main body;
a cooling medium that is connected to the other end of the thermal conduction member; and
a cooling source container that retains the cooling medium;
wherein the microprobe main body has a hollow tube part from a distal end to a base thereof, and a liquefied gas passes through the tube part and is discharged from the distal end of the microprobe main body.

* * * * *